(12) United States Patent
Gregory et al.

(10) Patent No.: US 9,656,050 B2
(45) Date of Patent: *May 23, 2017

(54) HEMORRHAGE CONTROL DEVICES AND METHODS

(71) Applicant: Oregon Biomedical Engineering Institute, Wilsonville, OR (US)

(72) Inventors: Kenton W. Gregory, Portland, OR (US); Lauryn L. Baranowski, Selah, WA (US); Arjun Kalyanpur, Edison, NJ (US); Seanna Vine, Newburyport, MA (US); Grant Blackwell, Bristol (GB); Benjamin Margolis, San Bruno, CA (US); Steven Dell, Carlsbad, CA (US)

(73) Assignee: Oregon Biomedical Engineering Institute, Wilsonville, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/475,281

(22) Filed: Sep. 2, 2014

(65) Prior Publication Data

US 2015/0057696 A1 Feb. 26, 2015

Related U.S. Application Data

(63) Continuation of application No. 12/773,680, filed on May 4, 2010, now Pat. No. 8,828,050.

(Continued)

(51) Int. Cl.
*A61M 29/02* (2006.01)
*A61L 15/42* (2006.01)
(Continued)

(52) U.S. Cl.
CPC ....... *A61M 29/02* (2013.01); *A61F 13/00008* (2013.01); *A61F 13/00025* (2013.01);
(Continued)

(58) Field of Classification Search
CPC ........ A61L 15/42; A61L 15/425; A61L 15/44; A61L 2400/04; A61F 13/0008;
(Continued)

(56) References Cited

U.S. PATENT DOCUMENTS 1,785,831 A 12/1930 Edmundson
2,858,830 A 11/1958 Robins
(Continued)

FOREIGN PATENT DOCUMENTS

EP 2319471 A2 5/2011
WO 00/29484 5/2000
(Continued)

OTHER PUBLICATIONS

Krause, David, "Proposal to Reclassify the Absorbable Hemostatic Agent Device, Memo to General and Plastic Surgery Devices Panel Members," Food and Drug Administration, Jun. 4, 2002; pp. 1-8.
(Continued)

*Primary Examiner* — Julian W Woo
*Assistant Examiner* — Shaun L David
(74) *Attorney, Agent, or Firm* — Schwabe, Williamson & Wyatt, P.C.

(57) ABSTRACT

Embodiments herein comprise a hemostatic composition comprising a plurality of liquid expandable articles capable of expanding upon contact with a liquid. A suitable composition comprises a plurality of liquid-expandable articles that may be mechanically uncoupled from one another and therefore may be capable of moving independently from one another. The plurality of liquid-expandable articles may comprise a compressed material capable of a high-degree of expansion upon liquid contact.

6 Claims, 10 Drawing Sheets

Related U.S. Application Data

(60) Provisional application No. 61/215,377, filed on May 4, 2009, provisional application No. 61/277,117, filed on Sep. 18, 2009, provisional application No. 61/310,075, filed on Mar. 3, 2010.

(51) Int. Cl.
  *A61L 15/44* (2006.01)
  *A61F 13/00* (2006.01)
  *A61F 13/36* (2006.01)
  *A61F 13/44* (2006.01)
  *A61L 24/00* (2006.01)

(52) U.S. Cl.
  CPC .. *A61F 13/00034* (2013.01); *A61F 13/00063* (2013.01); *A61F 13/36* (2013.01); *A61F 13/44* (2013.01); *A61L 15/425* (2013.01); *A61L 15/44* (2013.01); *A61L 24/0015* (2013.01); *A61F 2013/00106* (2013.01); *A61F 2013/00472* (2013.01); *A61L 2300/418* (2013.01); *A61L 2300/44* (2013.01); *A61L 2400/04* (2013.01); *A61M 2205/04* (2013.01)

(58) Field of Classification Search
  CPC .......... A61F 13/00034; A61F 13/00063; A61F 13/36; A61F 2013/00106; A61F 2013/00463; A61F 2013/00468; A61F 2013/00472
  See application file for complete search history.

(56) References Cited

U.S. PATENT DOCUMENTS

| | | |
|---|---|---|
| 5,383,891 A | 1/1995 | Walker |
| 5,584,827 A * | 12/1996 | Korteweg ........ A61B 17/12022 604/11 |
| 6,027,471 A | 2/2000 | Fallon et al. |
| 6,964,658 B2 | 11/2005 | Ashby et al. |
| 7,709,631 B2 | 5/2010 | Harris |
| 2003/0013989 A1 * | 1/2003 | Obermiller ...... A61B 17/12022 600/567 |
| 2003/0095997 A1 | 5/2003 | Ruszczak et al. |
| 2003/0202970 A1 | 10/2003 | Liu et al. |
| 2004/0013715 A1 | 1/2004 | Wnek et al. |
| 2004/0122350 A1 | 6/2004 | Zhong et al. |
| 2006/0004408 A1 | 1/2006 | Morris et al. |
| 2006/0173492 A1 | 8/2006 | Akerfeldt et al. |
| 2006/0233869 A1 | 10/2006 | Looney et al. |
| 2007/0014862 A1 | 1/2007 | Pameijer et al. |
| 2007/0021703 A1 | 1/2007 | McCarthy |
| 2007/0100271 A1 | 5/2007 | Shimanuki |
| 2007/0148161 A1 | 6/2007 | Delmotte |
| 2007/0255238 A1 | 11/2007 | Cochrum et al. |
| 2008/0071207 A1 | 3/2008 | DeLuis et al. |
| 2009/0226391 A1 | 9/2009 | Roberts et al. |
| 2010/0129427 A1 | 5/2010 | Hen |
| 2012/0209232 A1 | 8/2012 | Barofsky |
| 2014/0142523 A1 | 5/2014 | Steinbaugh |

FOREIGN PATENT DOCUMENTS

| | | |
|---|---|---|
| WO | 02/22059 | 3/2002 |
| WO | 2010/129587 A1 | 11/2010 |
| WO | 2012/112797 A2 | 2/2013 |

OTHER PUBLICATIONS

Natuno, T., et al., "New Collagen Topical Hemostatic Agent-Comparative Evaluation in Experimental Animal Wounds," Jpn J Artif Organs, 1990, vol. 19, No. 3, pp. 1235-1238.

* cited by examiner

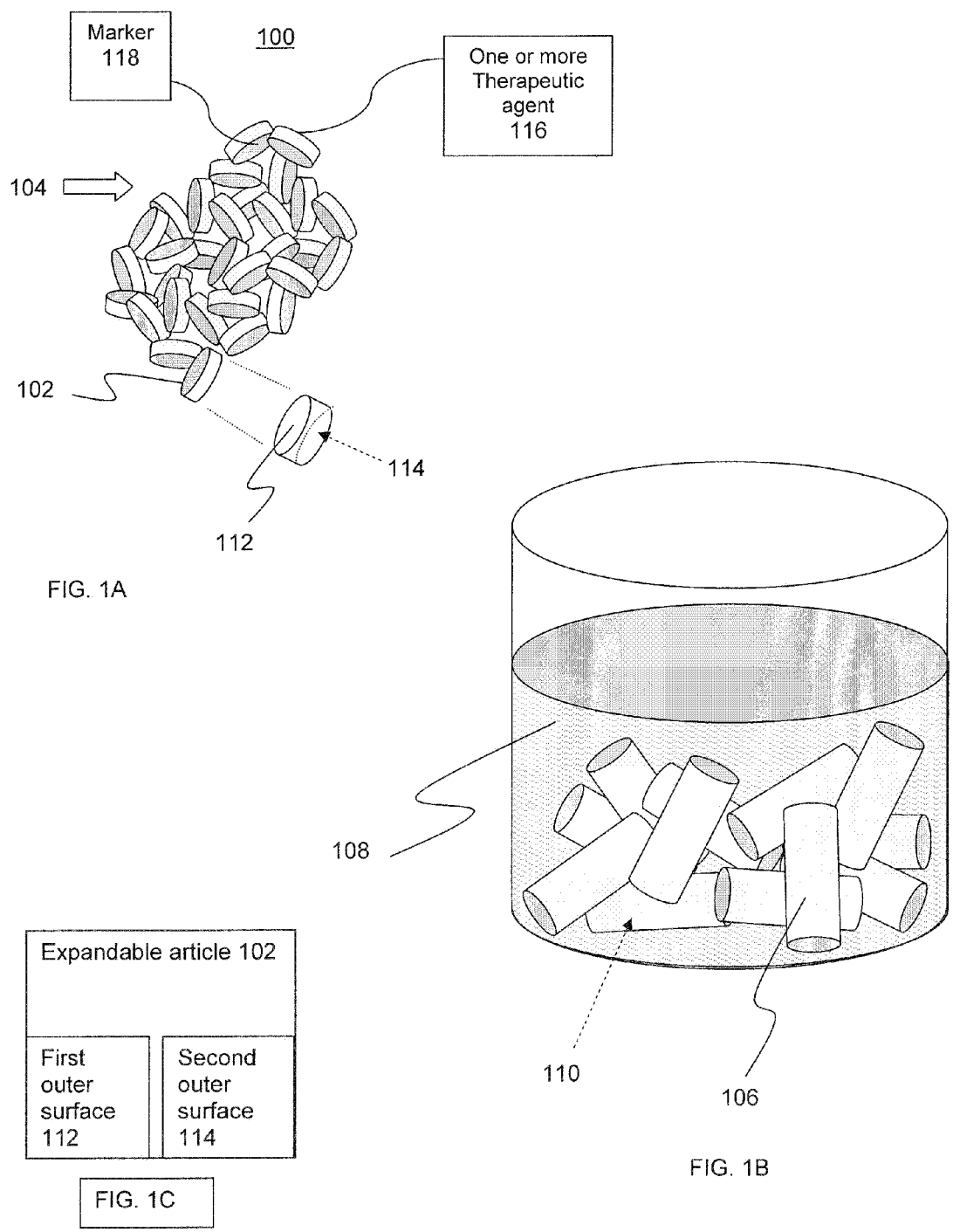

HEMORRHAGE CONTROL DEVICES AND METHODS

RELATED APPLICATIONS

This application is a continuation of U.S. patent application Ser. No. 12/773,680, now U.S. Pat. No. 8,828,050 (issued on Sep. 9, 2014), filed May 4, 2010, which claims the benefit of U.S. Provisional Application No. 61/215,377, filed May 4, 2009, U.S. Provisional Application No. 61/277,117, filed Sep. 18, 2009, and U.S. Provisional Application No. 61/310,075, filed Mar. 3, 2010, the contents of all of which are incorporated herein by reference in their entireties.

FEDERALLY SPONSORED RESEARCH OR DEVELOPMENT

This invention was made with United States government support pursuant to various contracts from the United States Special Operations Command. The United States may have certain rights to this invention.

TECHNICAL FIELD

Embodiments of the present invention relate to methods, compositions and devices for controlling bleeding and treating wounds.

BACKGROUND

A leading cause of preventable battlefield death is non-compressible, intracavitary bleeding. Projectiles from weapons and improvised explosive devices frequently create small entrance wounds having limited or no visibility to the sites of non-compressible, intracavitary bleeding. Although several wound dressing technologies are being marketed to control aggressive hemorrhages from severe external injuries, these devices are particularly ineffective against narrow-entry wounds and the survival of the soldier is entirely dependent on immediate access to blood products and emergent surgical repair.

A principal method for treating bleeding wounds is to stop the flow of blood by applying pressure with a bandage to facilitate formation of a clot. Current wound dressings are often too stiff and too rigid to fit into a narrow space of a cavity wound or, if sufficiently pliable, do not adequately conform to irregular tissues geometries to cause rapid and effective hemostasis.

Granular and powder based hemostatic products have been employed to address the deficiency of current wound dressing for non-compressible wounds, however, these products also have significant drawbacks. Hemostats in the form of powders, particulates or granules pose an unacceptable risk in forming emboli, are difficult to deploy in austere environments (e.g., environments that include wind, darkness, etc.), are susceptible to washing or migration away from the wound site, and are difficult to retrieve from the wound site at a place of definitive care. Additionally, granular and powder based hemostatic products are difficult to handle because they may have high electrostatic charge causing them to stick to instruments, gloves and tissues, thus preventing adequate penetration into irregular wound cavities. Also, in windy environments, powders or granules may be very difficult to get into the wound and may actually blow back into a caregiver's eyes. Powder or granule based hemostats also exhibit a lack of physical cohesion, making them unable to sufficiently withstand the chaotic fluid environments created by severe, high pressure bleeding. Thus, these granular and powder based hemostats may simply wash away before effectively contributing to hemostasis.

Accordingly, there remains a need for a more effective way to treat non-compressible hemorrhagic injuries.

SUMMARY

In a first aspect, the invention is directed to a hemostatic composition comprising a plurality of liquid expandable articles capable of expanding upon contact with a liquid.

In a second aspect, the invention is directed to a medical device comprising the composition of the first aspect with an applicator. The applicator facilitates the storage, handling and deployment of the composition of the first aspect.

In a third aspect, the invention is directed toward a method to effect rapid hemostatic response and control hemorrhage by introducing the composition of the first aspect into a bleeding wound cavity.

In a fourth aspect, the invention provides a method of preparing a composition in accordance with the first aspect of the invention.

In a fifth aspect, the invention provides a method of preparing a medical device in accordance with the second aspect of the present invention.

The invention is also directed to, in combination, a living being having a body with a wound defining a cavity with a volume bounded by a surface through which blood is flowing into the cavity, the cavity having an entry opening that is in communication with the cavity; and a plurality of expandable articles that each have a starting volume and a second volume that is greater than the starting volume, the plurality of expandable articles with the starting volume deliverable through the entry opening into the cavity and upon being exposed to fluid in the cavity expanded to the second volume, the plurality of expandable articles within the cavity and expanded to the second volume collectively inducing hemostasis.

BRIEF DESCRIPTION OF THE DRAWINGS

Embodiments of the present invention will be readily understood by the following detailed description in conjunction with the accompanying drawings. The present invention will be described by way of exemplary embodiments, but not limitations, illustrated in the accompanying drawings in which like references denote similar elements, and in which:

FIGS. 1A-1C illustrate embodiments of a hemostatic composition in accordance with the first aspect of the present invention.

DETAILED DESCRIPTION OF EMBODIMENTS OF THE INVENTION

Figure 2A:
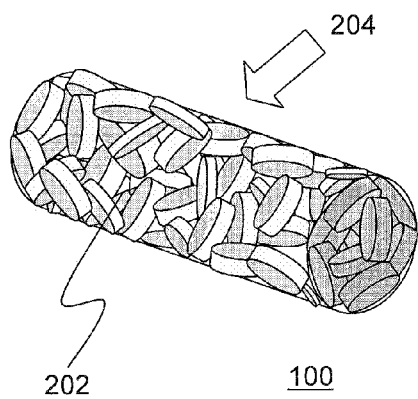
FIGS. 2A-2B illustrate further embodiments of a hemostatic composition in accordance with the first aspect of the present invention.

In the following detailed description, reference is made to the accompanying drawings which form a part hereof wherein like numerals designate like parts throughout, and in which is shown by way of illustration embodiments in which the invention may be practiced. It is to be understood that other embodiments may be utilized and structural or logical changes may be made without departing from the scope of the present invention. Therefore, the following detailed description is not to be taken in a limiting sense, and the scope of embodiments in accordance with the present invention is defined by the appended claims and their equivalents.

Various operations may be described as multiple discrete steps in turn, in a manner that may be helpful in understanding embodiments of the present invention; however, the order of description should not be construed to imply that these operations are order dependent.

The description may use the phrases "in an embodiment," or "in embodiments," which may each refer to one or more of the same or different embodiments. Furthermore, the terms "comprising," "including," "having," and the like, as used with respect to embodiments of the present invention, are synonymous. Additionally, the various embodiments of the present invention may be combined in any suitable manner.

In various embodiments of the invention, hemostatic compositions and devices, as well as methods for manufacturing such compositions and devices, are provided. In addition, various embodiments include methods for treating hemorrhagic injuries.

In the following description, unless further particularized or otherwise noted, the term "liquid expandable" is intended to refer to any material or substance that expands upon contact with a liquid.

In a first aspect, the invention is directed to a hemostatic composition comprising a plurality of liquid expandable articles capable of expanding upon contact with a liquid. FIG. 1A illustrates selected aspects of a hemostatic composition in accordance with an embodiment of the present invention. As shown, composition 100 includes liquid expandable articles 102, which are combined to form a plurality of liquid-expandable articles 104.

FIG. 1B depicts how each liquid-expandable article 102 is capable of expanding into an expanded article 106 upon contact with a liquid 108. It follows that the plurality of liquid expandable articles 104 is capable of expanding into a plurality of expanded articles 110 upon contact with liquid 108. In various embodiments, liquid 108 may be an aqueous solution, such as a bodily fluid. For example, liquid 108 may be blood.

According to various embodiments of the present invention, composition 100 comprises a plurality of liquid-expandable articles 104 that may be mechanically uncoupled from one another and therefore may be capable of moving independently from one another. Without limiting the invention to any particular theory, this quality may permit the liquid-expandable articles 102 to pass through narrow wound openings and to spread into irregular wound crevices, gaps and fissures.

According to embodiments of the present invention, plurality of liquid expandable articles 104 may comprise at least 3 liquid expandable articles 102. In another embodiment, plurality of liquid expandable articles 104 comprises at least 10 liquid expandable articles 102. In yet another embodiment, plurality of liquid expandable articles 104 comprises at least 50 liquid expandable articles 102. In yet another embodiment, plurality of liquid expandable articles 104 comprises at least 100 liquid expandable articles 102.

In embodiments of the present invention, the volume of each liquid-expandable article 102 may be from 0.7 mm$^3$ to 7000 mm$^3$. Without limiting the invention to any particular theory, articles in this volume range may be advantageous because they are small enough to flow freely through narrow wound entries, yet large enough to avoid becoming emboli via movement into torn or perforated blood vessels. Articles in this volume range are easy to find and retrieve from the wound site at a place of definitive repair. In addition, liquid-expandable articles 102 in this volume range are capable of expanding into expanded articles 106 that are large enough to maintain position in a wound cavity in the presence of a high-flow arterial bleed. In various embodiments, the volume of each liquid-expandable article 102 may be greater than 1 mm$^3$. In various embodiments, the volume of each liquid-expandable article 102 may be greater than 5 mm$^3$. In various embodiments, the volume of each liquid-expandable article 102 may be greater than 10 mm$^3$. In various embodiments, the volume of each liquid-expandable article 102 may be greater than 50 mm$^3$. In various embodiments, the volume of each liquid-expandable article 102 may be greater than 100 mm$^3$. In various embodiments, plurality of liquid-expandable articles 104 may have liquid-expandable articles 102 comprising a mixture of sizes.

According to various embodiments, the expanded articles 106 have a volume greater than the liquid-expandable articles 102. In various embodiments, the average volume ratio of liquid-expandable articles 102 to expanded articles 106 is at least 4×. In other embodiments, the average volume ratio of liquid-expandable articles 102 to expanded articles 106 is at least 8×. In other embodiments, the average volume ratio of liquid-expandable articles 102 to expanded articles 106 is at least 10×. In other embodiments, the average volume ratio of liquid-expandable articles 102 to expanded articles 106 is at least 12×.

In various embodiments of the present invention, liquid-expandable articles 102 may be capable of expanding to 80% or greater of their maximum expansion capacity in 30 seconds or less following immersion in liquid 108. In other embodiments, liquid-expandable articles 102 may be capable of expanding to 80% or greater of their maximum expansion capacity in 10 seconds or less following immersion in liquid 108. In other embodiments, liquid-expandable articles 102 may be capable of expanding to 80% or greater of their maximum expansion capacity in 5 seconds or less following immersion in liquid 108.

The plurality of liquid-expandable articles 104 may include liquid-expandable articles 102 of one or more predetermined shapes. The shape of liquid-expandable articles 102 may influence the ability of the articles to flow freely through narrow wound entries and to expand, fill, partially fill and conform to a wound cavity. In addition, the shape may assist expanded articles 106 in retaining a desired position in the wound cavity. In FIG. 1, liquid expandable articles 102 are depicted as a cylindrical shape. This notwithstanding, the predetermined shape of liquid expandable articles 102 may include other round, triangular, rectangular, hexagonal conical or octagonal elements. In various embodiments, predetermined shapes having multiple projections (e.g., a star) may be used. In other embodiments, the plurality of liquid-expandable articles 104 may comprise liquid-expandable articles 102 with haphazard, random, irregular or jagged shapes. In various embodiments, plurality of liquid-expandable articles 104 may comprise liquid-expandable articles 102 of two or more predetermined shapes. In other embodiments, plurality of liquid-expandable articles 104 may have liquid-expandable articles 102 comprising a mixture of predetermined shapes and/or irregular shapes.

As shown in FIG. 1C, the predetermined shape of liquid-expandable articles 102 may define any shape having first major outer surface 112 and a second major outer surface 114. In various embodiments, the average distance between the outer surfaces may be from 0.5 mm to 20 mm. In various embodiments of the present invention, the average distance between a first major outer surface 112 and a second major outer surface 114 may be from 1 mm to 10 mm. For such embodiments, the average distance between the first major outer surface 112 and the second major outer surface 114 may be from 2 mm to 5 mm.

According to various embodiments of the present invention, liquid-expandable articles 102 may be substantially in the form of a disk or cylinder. For such embodiments, the average diameter of the first major outer surface 112 and the second major outer surface 114 may be from 1 mm to 20 mm. The average diameter of the first major outer surface 112 and the second major outer surface 114 may be from 5 mm to 10 mm. In various embodiments, composition 100 may comprise liquid-expandable articles 102 having the same average diameter or a mixture liquid-expandable articles 102 having different average diameters.

In various embodiments of the present invention, the liquid-expandable articles 102 may comprise an absorbent material including, but not limited to, a sponge or fibrous material. In various embodiments of this aspect, the absorbent material may comprise a polysaccharide such as, but not limited to, cellulose, starch, chitin or chitosan. In various embodiments of the present invention, liquid-expandable articles 102 may be biodegradable and/or bioabsorbable. In some embodiments, the liquid-expandable articles 102 may not comprise oxidized cellulose. In various embodiments, the absorbent material may comprise synthetic sponges such as, but not limited to, various polyvinyl alcohol (PVA) polymers and derivatives thereof having desirable physical and mechanical properties.

In various embodiments, liquid-expandable articles 102 may comprise a compressed material. For these embodiments, and without limiting this invention as to any particular theory, the compressed material, when hydrated, may rapidly expand in an effort to assume its pre-compression dimensions. In this way, liquid-expandable articles 102 may store additional mechanical energy in a compressed state, as compared to the non-compressed state, that is released when exposed to liquid 108, thus causing liquid-expanding articles 102 to quickly expand without using exogenous gases, liquids or pressure. The absorbent material can be compressed by heat compression or any other suitable method known in the art.

In various embodiments of this aspect, composition 100 may further comprise one or more therapeutic agents 116. In an embodiment, the liquid-expandable articles 102 may be impregnated with the one or more therapeutic agents 116. In another embodiment, the liquid-expandable articles 102 may be suffused with one or more therapeutic agents 116. In another embodiment, the liquid-expandable articles 102 may be coated with one or more therapeutic agents 116. In yet another embodiment, the one or more therapeutic agents 116 may be dispersed throughout liquid-expandable articles 102.

The one or more therapeutic agents 116 may be selected from the group consisting of analgesics, steroids, antihistamines, anesthetics, bactericides, disinfectants, fungicides, vasoconstrictors, chemotherapeutic drugs, antibiotics, keratolytics, cauterizing agents, antiviral drugs, epidermal growth factor, fibroblast growth factors, transforming growth factors, glycoproteins, fibrinogen, fibrin, humectants, preservatives, lymphokines, cytokines, odor controlling materials, vitamins, and clotting factors.

In various embodiments, the one or more therapeutic agents 116 may include hemostatic agent(s). For example, the one or more therapeutic agents 116 may include chitosan or a derivative of chitosan. In other embodiments, the one or more therapeutic agents 116 may include kaolin. In other embodiments of the present invention, the one or more therapeutic agents 116 may be selected from the group consisting of diatomaceous earth, silica, clays, minerals, attapulgite, bentonite, zeolite, and bioactive glasses.

According to various embodiments, the one or more therapeutic agents 116 may include an inorganic salt. Examples of an inorganic salt include, but are not limited to, a divalent ion selected from the group consisting of zinc, copper, magnesium, calcium and nickel, as well as CaO, CaCl2, AgN03, Ca(N03)2, Mg(N03)2, Zn(N03)2, NH4N03, AgCl, Ag2O, zinc acetate, magnesium acetate, calcium citrate, zinc citrate, magnesium citrate, magnesium chloride, magnesium bromide, zinc chloride, zinc bromide, calcium bromide, calcium acetate and calcium phosphate.

In various embodiments of the present invention, each liquid-expandable article 102 may comprise a marker 118 for identifying the location of the articles in a wound and facilitating removal of the articles from the wound. For such embodiments, marker 118 may comprise a radio-frequency identification (RFID) tag. In other embodiments, marker 118 may comprise a radiopaque material. For example, each liquid-expandable article may include a radiopaque bead, ball, sphere, wire or strip imbedded within each liquid-expandable article 102. In other embodiments, liquid-expandable articles 102 may be suffused with a radiopaque material. In yet another embodiment, at least a portion of each liquid-expandable article 102 may be coated with a radiopaque material.

Figure 2B:
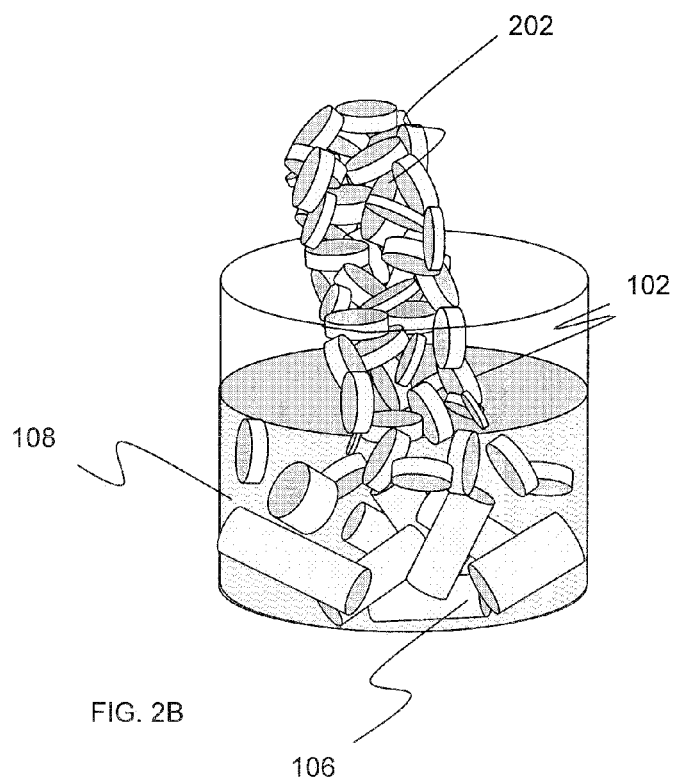

FIG. 2 illustrates a hemostatic composition in accordance with a further embodiment of the present invention. As illustrated, composition 100 may be in the form of a composite article 202, wherein composite article 202 comprises plurality of liquid-expandable articles 104 which have been further compressed together. For such embodiments, composite article 202 is capable of quickly disassociating into individual liquid expandable articles 102 upon contact with liquid 108. Composite article 202 may advantageously increase the number and density of liquid-expandable articles 102 that can be stored/maintained prior to use and allow for an increase in the number of liquid-expandable articles 102, and ultimately expanded articles 106, that may be delivered into a wound cavity.

Figure 3:
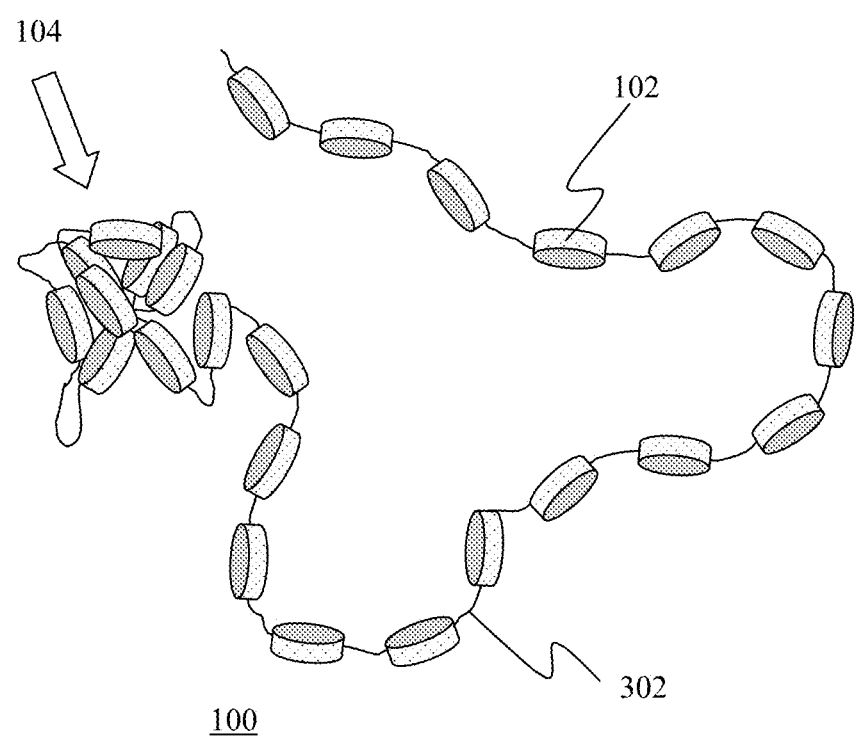
FIG. 3 illustrates further embodiments of a hemostatic composition in accordance with the first aspect of the present invention.

According to additional embodiments of this aspect, composition 100 may comprise a plurality of liquid expandable articles 104 that are coupled to one another to assist with removal of expanded articles 106 from the wound. For example, as illustrated in FIG. 3, composition 100 may comprise a plurality of liquid-expandable articles 104 that are coupled to one another with a string 302. For example, liquid-expandable articles 102 may be threaded onto string 302. In other embodiments, liquid expandable articles 102 may be affixed to string 302. The liquid-expandable articles 102 may be arranged in any suitable orientation on the string 302 so long as string 302 does not impede the expansion of liquid expandable articles 102 once they are in contact with liquid 108. For such embodiments, liquid-expandable articles are arranged on string 302 in a way that allows composition 100 to pass through narrow wound openings and liquid-expandable articles 102 to spread into irregular wound crevices, gaps and fissures.

The attachment of the liquid expandable articles 102 to string 302 aids in the recovery of expanded articles 106 from the wound cavity, once the patient reaches a place of definitive care. The caregiver simply needs to pull the string 302 out of the wound cavity and the plurality of liquid expanded articles 110 is simultaneously removed.

Figure 4:
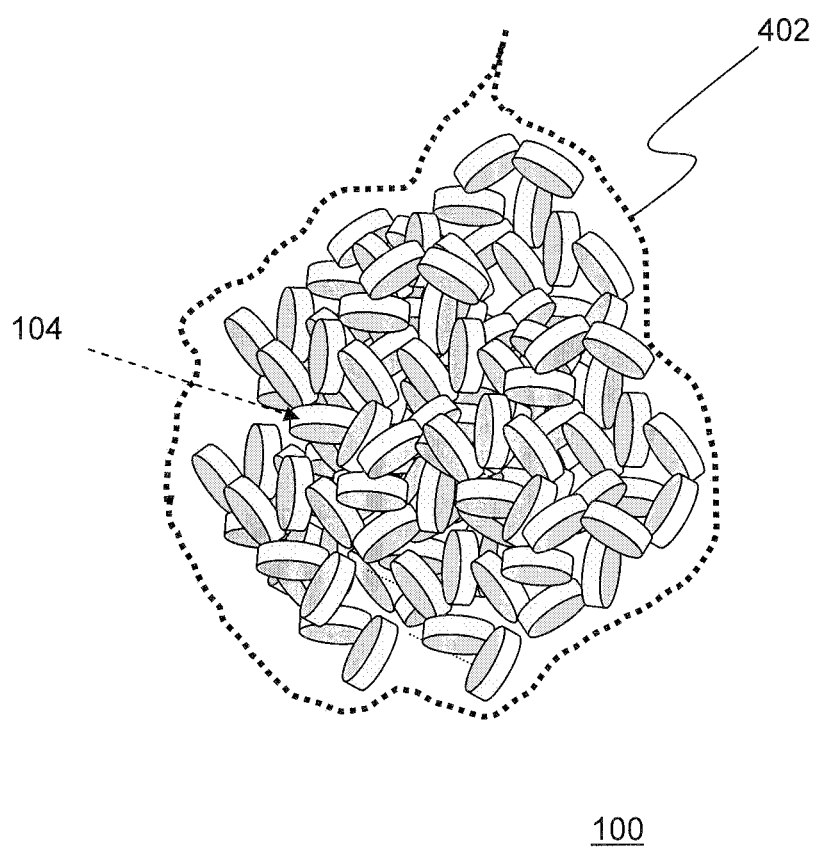
FIG. 4 illustrates a device according to the second aspect of the invention.

FIG. 4 represents another embodiment of composition 100, in accordance with the first aspect. In embodiments of this aspect, plurality of liquid-expandable articles 104 is positioned in a porous, expandable bag 402. Bag 402 is employed to facilitate the delivery of liquid-expandable articles 102 and removal of expanded articles 106. For example, bag 402 comprising composition 100 may be applied to a bleeding wound. Once the injured individual is transported from a field environment to a place of definitive medical care, the bag 402, and thus the expanded articles 106 therein, can simply be removed from the wound cavity so that care can be administered. For such embodiments, bag 402 is sufficiently flexible, porous and expandable to allow composition 100 to pass through narrow wound openings and to allow liquid-expandable articles 102 to expand in to expandable articles 106.

Figure 5:
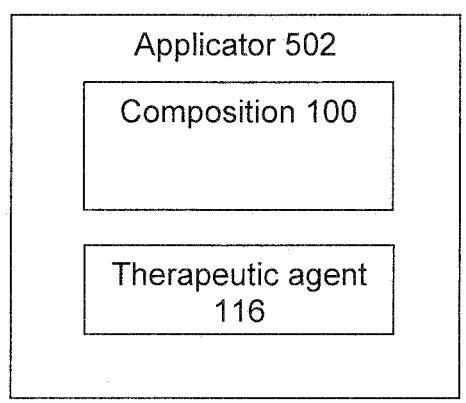
FIG. 5 illustrates embodiments of a device according to the second aspect of the invention.

In a second aspect, the invention is directed to a medical device comprising the composition of the first aspect and an applicator. The applicator facilitates the storage, handling and application of the composition of the first aspect. Referring now to FIG. 5, wherein a block diagram illustrating a medical device 500 comprising composition 100 in accordance with the present invention, is shown. As illustrated, medical device 500 includes composition 100 positioned in an applicator 502. Applicator 502 is employed to facilitate the storage, handling and/or application of composition 100.

In some embodiments, medical device 500 may further include one or more therapeutic agents 116 positioned in an applicator 502. In one form, the one or more therapeutic agents 116 may be dispersed throughout device 500. For such embodiments, the one or more therapeutic agents 116 may be detached from composition 100.

Figure 6:
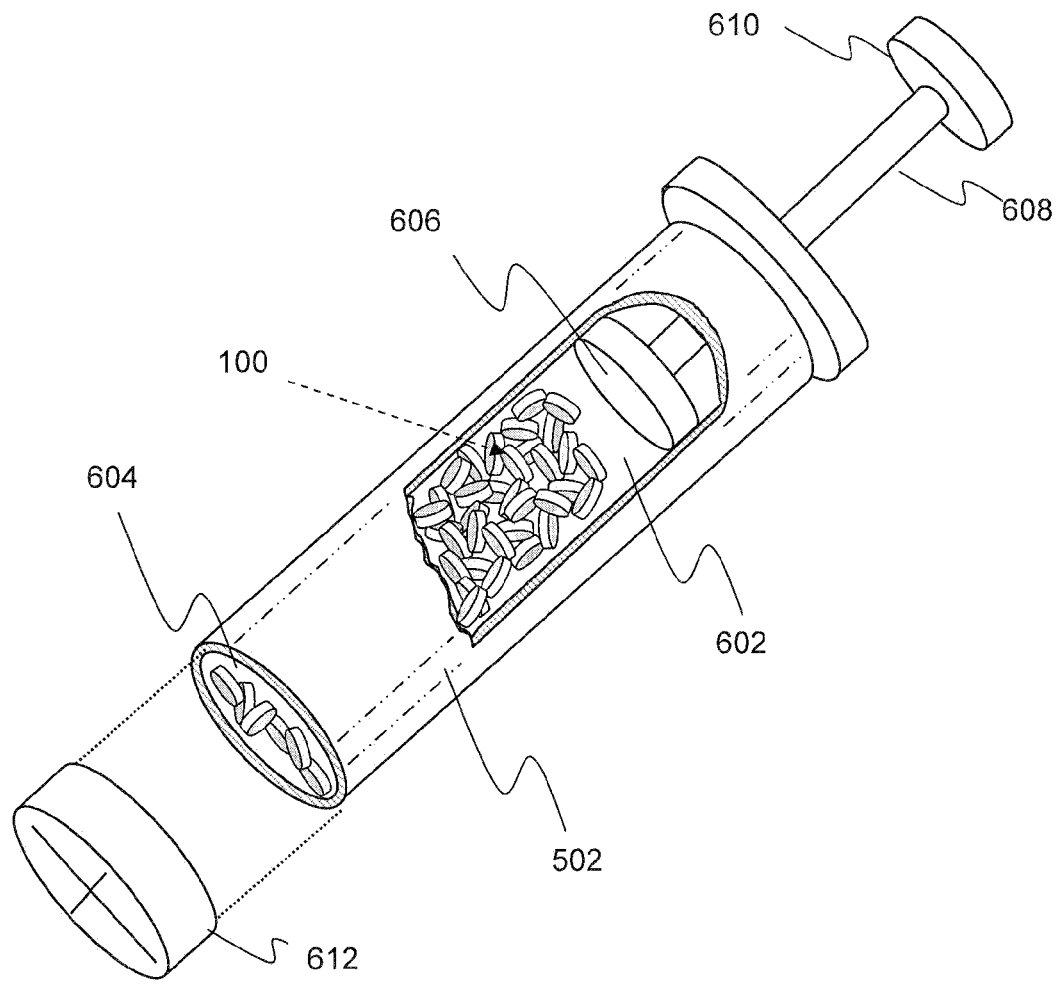
FIG. 6 illustrates further embodiments of a device according to the second aspect of the invention.

FIG. 6 illustrates one form of medical device 500 in accordance with embodiments of the present invention. As shown, applicator 502 includes a receptacle 602 with an output end 604 and a moveable piston 606 positioned in receptacle 602. Composition 100 is positioned in receptacle 602. According to various embodiments, receptacle 602 may be a tube.

In one form, receptacle 602 may comprise a plastic. For example, receptacle 602 may comprise PEEK, PEKK, Polyetherimide (PEI), Polyethersulfone (PES), Polyetherimide (PEI), Polyimide (TPI), FEP, FEP 100, ETFE, ETFE 207, ECTFE, PFA or PTFE. In other embodiments, receptacle 602 may comprise a filled plastic or a polymer composite.

Moveable piston 606 is employed to facilitate the ejection of the plurality of liquid-expandable articles 104 from receptacle 602 through output end 604. In an embodiment, moveable piston 606 may be coupled to shaft 608, which has a handle 610. In other embodiments, moveable piston 606 may be coupled to a spring or other similar force-applying element.

In accordance with various embodiments, medical device 500 may include a valve 612 coupled to the receptacle 602 at output end 604. Valve 612 is employed to prevent the premature exit of liquid-expandable articles 102 from receptacle 602, as well as impede the flow of liquid 108 into receptacle 602 prior to the ejection of liquid-expandable articles.

In various embodiments of this aspect, medical device 500 may be included in a kit. A typical kit would comprise medical device 500 and instructions, such as a product insert or label, directing the user to prepare and administer composition 100.

In a third aspect, the present invention is directed toward a method to effect rapid hemostatic response and hemorrhage control by applying the composition of the first aspect to a bleeding wound.

Figure 7:
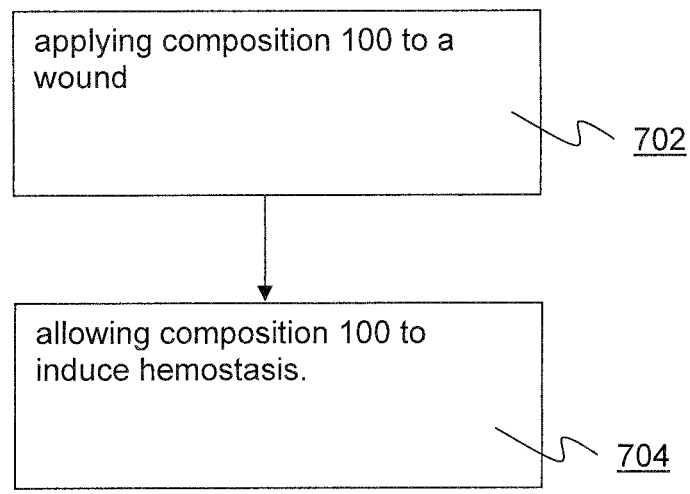
FIG. 7 is illustrative of treating a wound with a composition according to the first aspect of the invention.

FIG. 7 is a block diagram depicting a method for treating hemorrhagic injuries in accordance with embodiments of the present invention. As illustrated, at 702, composition 100 is applied to a wound. At 704, the plurality of liquid expandable sponges 104 are allowed to induce hemostasis. For example, the plurality of liquid-expandable articles 104 may be delivered into a wound cavity, allowed to contact blood within the cavity and subsequently expand into expanded articles 106, which conform to a shape defined by at least a portion of the wound cavity.

Applying composition 100 to a wound may comprise applying the composition 100 by hand or by employing medical device 500. If a composite article 202 is being used, the plurality of liquid expandable articles 104 may be manually separated to uncouple the liquid-expandable articles 102 prior to applying the plurality of liquid-expandable articles 104 to the wound. In various embodiments, composite article 202 may disassociate into individual articles upon contact with liquid 108.

Exemplary wounds often arise from, but are not limited to, traumatic accidents, projectiles from weapons or improvised explosive devices which frequently create small entrance wounds having limited or no visibility to the sites of non-compressible, intra-cavitary bleeding. Such wounds can result in an arterial puncture, a venous puncture, an arterial laceration and/or a venous laceration.

Each wound can have a unique size and/or shape. Often, the extent of the tissue damage cannot be determined until emergent care can be provided. The use of a plurality of liquid-expandable articles 104 allows for the treatment of several wound types without the need to predetermine the size and/or shape of a single expandable article (i.e., a single expandable plug or pellet) as required to promote hemostasis.

Figures 8A, 8B:
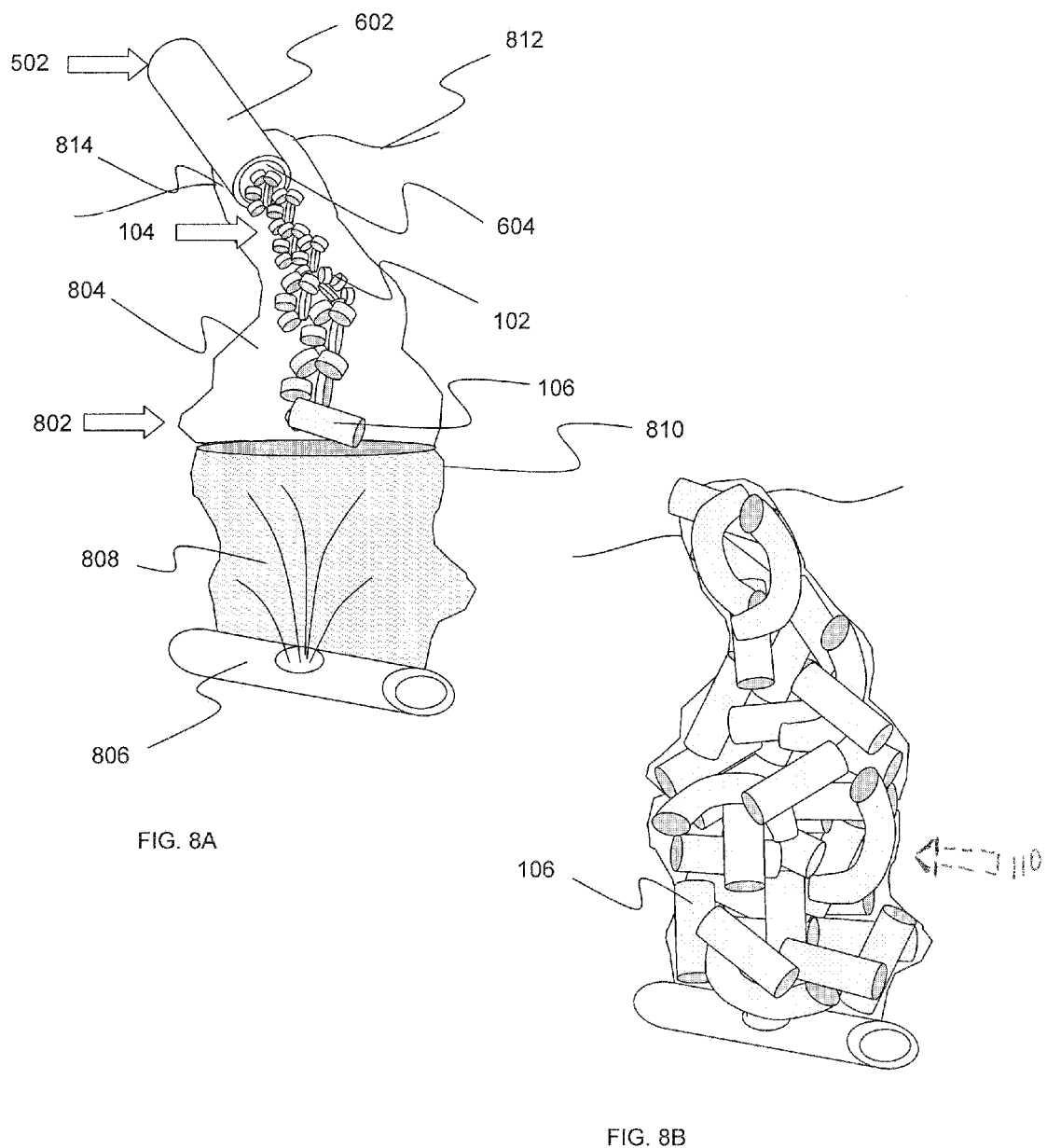
FIGS. 8A-8B illustrate a method for treating a bleeding wound employing the hemostatic compositions in accordance with embodiments of the first aspect of the present invention.

FIG. 8 illustrates a method for treating hemorrhagic injuries in a living being 812 employing the medical device of FIG. 5. As illustrated, composition 100 may be applied to a wound 802 using medical device 500 (FIG. 8A). For such embodiments, plurality of liquid-expandable articles 104 may be ejected from receptacle 602 through output end 604. In an exemplary embodiment, wound 802 defines a cavity 804 with an opening 814 and a cavity boundary 810 and includes at least one bleeding vessel 806. Once in the wound, liquid-expandable articles 102 contact blood 808 and expand into a expanded articles 106. As shown in FIG. 8B expanded articles 106 fill cavity 804 and induce hemostasis.

Figure 9:
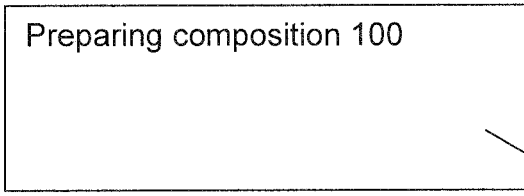
FIG. 9 is illustrative of the preparation of a composition according to the first aspect of the invention.

In a fourth aspect, the invention provides a method of preparing a composition in accordance with the first aspect of the invention. FIG. 9 generically depicts a method of manufacturing composition 100 in accordance with embodiments of the present invention. At 902, composition 100 may be prepared by forming an absorbant material into liquid-expandable articles which are combined to form a plurality of liquid-expandable articles.

For various embodiments, forming the absorbant material into a plurality of liquid-expandable articles may include compressing the absorbant material into a liquid-expandable material. This may be accomplished, for example, using conventional mechanical compression techniques well known to those skilled in the art. In other embodiments, compressing the absorbant material into a liquid-expandable material may comprise freeze-drying the absorbant material.

Forming the absorbant material into a plurality of liquid-expandable articles may include forming it into desirable shapes and sizes. For such embodiments, the liquid-expandable material may be cut using, for example, a die and press. The absorbant material may also be molded directly into desired shapes and sizes.

In various embodiments, the absorbant material may be formed into a plurality of liquid-expandable articles by extrusion, pelletization, briquetting, tabletting, or other methods familiar to those skilled in the art. Alternatively, the absorbant material may be mechanically crushed into irregular shaped lumps, with desirable size ranges to be separated out by a classifier.

The absorbant material may be combined with one or more therapeutic agents prior to, during or subsequent to being formed into liquid-expandable articles. The combining of absorbant material with one or more therapeutic agent may be performed by impregnating, suffusing, coating or dispersing the on or more therapeutic agents on or throughout the absorbant material. In an embodiment, the therapeutic agent may be sprayed onto the absorbent material. In another embodiment, the absorbent material may be soaked in a therapeutic agent solution. The one or more therapeutic agents may be selected from the group disclosed above.

In further embodiments of the present invention, a marker may be applied to each of the liquid-expandable articles. This may be accomplished in a number of ways. For example, the marker may be imbedded in the absorbant material prior to forming the absorbant material into liquid-expandable articles. Alternatively, the marker may be imbedded in the liquid-expandable articles during or following a formation step. In another embodiment, a radiopaque material may be coated or suffused onto the absorbant material before, during or after formation of the liquid-expandable articles. For such embodiments, the marker may be selected from the markers disclosed above.

In further embodiments of the present invention, the plurality of liquid-expandable articles of composition 100 may be further compressed together to form the composite article 202.

Figure 10:
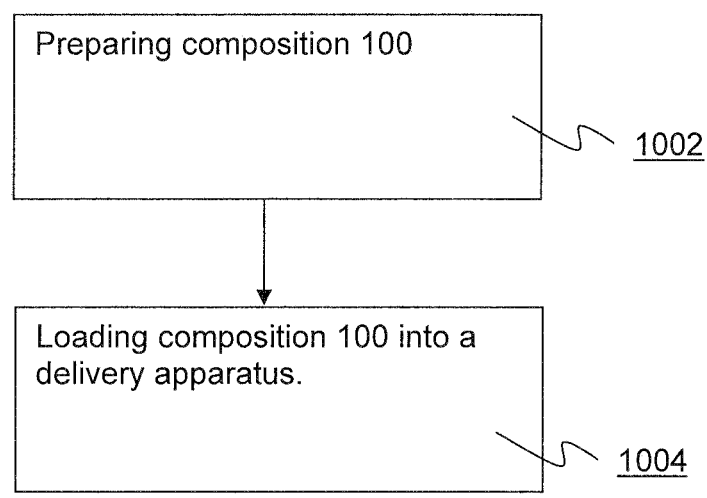
FIG. 10 is illustrative of preparing a device according to the second aspect of the invention.

In a fifth aspect, the invention provides a method of preparing a medical device in accordance with the second aspect of the present invention. FIG. 10 depicts a method of manufacturing a medical device 500 in accordance with embodiments of the present invention. At 1002, an absorbant material may be formed into composition 100. Once composition 100 has been prepared, it is loaded into an applicator 502 (Block 1004).

The invention is also directed to, in combination, a living being having a body with a wound defining a cavity with a volume bounded by a surface through which blood is flowing into the cavity, the cavity having an entry opening that is in communication with the cavity; and a plurality of expandable articles that each have a starting volume and a second volume that is greater than the starting volume, the plurality of expandable articles with the starting volume deliverable through the entry opening into the cavity and upon being exposed to fluid in the cavity expanded to the second volume, the plurality of expandable articles within the cavity and expanded to the second volume collectively inducing hemostasis.

The present invention is directed to a composition comprising a plurality of small, liquid-expandable articles that are configured to induce hemostasis when contacted with blood and can be applied in deep, irregular wounds. The plurality of liquid-expandable articles possess an ability, upon contact with blood, to rapidly expand in unison to form a pliable, shapeable, conformable and crevice-filling mass.

Without limiting the invention, this mass may exert gentle mechanical pressure on the surface of the wound, as well as interact with blood components to ultimately facilitate the formation of a fluid arresting coagulum within the wound cavity. The combination of mechanical pressure and enhanced clotting makes the composition able to curtail bleeding without the application of external compression. In other embodiments, liquid-expandable articles may be capable of expanding through a swelling mechanism.

Without limiting the invention, compositions of the invention may be advantageous for several reasons. Unlike devices that rely on deploying a single hemostatic article or mass (e.g., a single plug, cylinder or sheet), the liquid-expandable articles are sufficiently small to possess a fluid-like flow quality. This quality permits a plurality of liquid-expandable articles to be fed through narrow wound openings and to spread into irregular wound crevices, gaps and fissures. Available plugs or sheets are limited by having a fixed dimension, making it difficult to pass them into a small cavitary wound. On the other hand, the liquid-expandable articles are large enough to avoid performance drawbacks associated with granules or powders, such as high electrostatic charge, risk of forming emboli, lack of physical cohesion and difficulties associated with locating and surgically retrieving hemostatic material at a definitive care site.

Another advantage of the liquid-expandable articles as described herein is the ability to quickly expand into expanded articles. This allows the expanded articles to quickly fill the wound cavity and provide a nearly immediate hemostatic effect without the need for applying any external compression. Additional advantages associated with the present invention include improved positioning within the wound, improved tissue apposition and better conformation to intricate wound contours. The soft, pliable nature of the expanded articles, in connection with spring-like characteristics, permits the expanded articles to provide a gentle outward pressure within the wound cavity, without the need to apply excessive pressure that can compromise perfusion to local tissues. Because the expanded articles conform to the wound cavity, pressure is exerted multidirectionally to address all bleeding points. The ability to exert outward pressure against and closely conform to surrounding tissue surfaces helps the expanded articles maintain positioning within in the wound cavity in the face of high flow arterial bleeding and deformation during transport of the injured person; maximize the contact and application of material at the sources of bleeding; and ensure constant and gentle, yet effective, compression within the wound cavity (without creating harmful pressure points).

An additional advantage of the present invention is that it is adaptable to different wound sizes and shapes. If an initial dose of composition 100 is insufficient to fill the wound, the user may simply add more liquid-expandable articles 102 until the desired effect is achieved.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the present invention.

This application is intended to cover any adaptations or variations of the embodiments discussed herein. Therefore, it is manifestly intended that embodiments in accordance with the present invention be limited only by the claims and the equivalents thereof.

EXAMPLES

Example 1

The speed of expansion and degree of expansion of liquid-expandable articles were measured in saline.

Materials

Composition 1: Regenerated cellulose sponge blocks (3M, Minneapolis, Minn.)(190 mm×109 mm×50 mm) were washed, soaked in a chitosan solution (1% chitosan, 2% acetic acid), compressed and freeze dried. The dry, compressed blocks were die cut into 9.52 mm diameter cylinders.

Composition 2: Regenerated cellulose sponge blocks (3M, Minneapolis, Minn.) (190 mm×109 mm×50 mm) were washed, soaked in a chitosan solution (1% chitosan, 2% acetic acid), heat dried and compressed. The dry, compressed blocks were die cut into 9.52 mm diameter cylinders.

Composition 3: Regenerated cellulose sponge blocks (3M, Minneapolis, Minn.) (190 mm×109 mm×50 mm) were washed, heat dried and compressed. The dry, compressed blocks were die cut into 9.52 mm diameter cylinders.

Composition 4: Regenerated cellulose sponge blocks (Toray Fine Chemicals, Chiba, Japan) (190 mm×90 mm×50 mm) were washed, soaked in a chitosan solution (1% chitosan, 2% acetic acid), heat dried and compressed. The dry, compressed blocks were die cut into 9.52 mm diameter cylinders.

Methods

A large weigh boat with a ruler taped to it was filled with 22 mL of saline. The thickness of each sample was measured using calipers. Next, the sample was pressed onto a 27 gauge needle into the center of the top face of the test sample. A timer was started and the needle with the test sample attached was placed into the saline with the sample at the 0 cm mark on the ruler. The length of the sample articles were measure at 5, 20, and 60 seconds.

Results

Thickness at Time Intervals

Composition 1

|  | Time (s) | | | |
| --- | --- | --- | --- | --- |
|  | 0 | 5 | 20 | 60 |
| Average (cm) | 0.55 | 4.46 | 4.93 | 5.07 |
| Stdard Dev | 0.10 | 0.78 | 0.30 | 0.17 |

(n = 18)

Composition 2

|  | Time (s) | | | |
| --- | --- | --- | --- | --- |
|  | 0 | 5 | 20 | 60 |
| Average (cm) | 0.30 | 4.45 | 4.66 | 4.78 |
| Stdard Dev | 0.04 | 0.36 | 0.24 | 0.25 |

(n = 48)

Composition 3

|  | Time (s) | | | |
| --- | --- | --- | --- | --- |
|  | 0 | 5 | 20 | 60 |
| Average (cm) | 0.28 | 3.51 | 4.63 | 4.89 |
| Stdard Dev | 0.05 | 1.31 | 0.51 | 0.34 |

(n = 48)

Composition 4

|  | Time (s) | | | |
| --- | --- | --- | --- | --- |
|  | 0 | 5 | 20 | 60 |
| Average (cm) | 0.34 | 3.88 | 4.15 | 4.29 |
| Stdard Dev | 0.05 | 0.58 | 0.43 | 0.40 |

(n = 66)

Degree of Expansion

The degree of expansion is defined as the percentage of full expansion at a given time interval. More specifically:

$$\text{Degree of Expansion} = t_i/t_f$$

Where $t_i$ is the thickness at some time interval and $t_f$ is the final thickness. The final thickness is measured at the end of the experiment, outside of saline.

Composition 1

|  | Time | | | |
| --- | --- | --- | --- | --- |
|  | 0 | 5 | 20 | 60 |
| Average | 0.11 | 0.86 | 0.96 | 0.98 |
| Overall Stdard Dev | 0.02 | 0.14 | 0.05 | 0.02 |

(n = 16)

Composition 2

|  | Time | | | |
|---|---|---|---|---|
|  | 0 | 5 | 20 | 60 |
| Average | 0.06 | 0.93 | 0.98 | 1.00 |
| Overall Stdard Dev | 0.01 | 0.06 | 0.03 | 0.01 |

(n = 48)

Composition 3

|  | Time | | | |
|---|---|---|---|---|
|  | 0 | 5 | 20 | 60 |
| Ave | 0.11 | 0.71 | 0.95 | 1.00 |
| Std | 0.17 | 0.24 | 0.06 | 0.01 |

(n = 48)

Composition 4

|  | Time (s) | | | |
|---|---|---|---|---|
|  | 0 | 5 | 20 | 60 |
| Average | 0.08 | 0.90 | 0.97 | 1.00 |
| Overall Stdard Dev | 0.01 | 0.10 | 0.05 | 0.03 |

(n = 66)

Expansion Factor

The Expansion Factor is defined as a multiple of the original thickness at a given time interval. More specifically:

$$\text{Expansion Factor} = t_t/t_0$$

Where $t_t$ is the thickness (cm) and $t_0$ is the initial dry thickness measurement.

Composition 1

|  | Time (s) | | | |
|---|---|---|---|---|
|  | 0 | 5 | 20 | 60 |
| Average | 1.00 | 8.20 | 9.23 | 9.52 |
| Overall Stdard Dev | 0.00 | 1.37 | 1.66 | 1.74 |

(n = 16)

Composition 2

|  | Time (s) | | | |
|---|---|---|---|---|
|  | 0 | 5 | 20 | 60 |
| Average | 1.00 | 15.23 | 16.00 | 16.40 |
| Overall Stdard Dev | 0.00 | 1.79 | 1.79 | 1.73 |

(n = 48)

Composition 3

|  | Time (s) | | | |
|---|---|---|---|---|
|  | 0 | 5 | 20 | 60 |
| Ave (cm) | 1.00 | 10.98 | 15.24 | 16.23 |
| Overal Stdard Dev | 0.00 | 5.47 | 5.19 | 5.51 |

(n = 48)

Composition 4

|  | Time (s) | | | |
|---|---|---|---|---|
|  | 0 | 5 | 20 | 60 |
| Average (cm) | 1.00 | 11.52 | 12.39 | 12.82 |
| Overall Stdard Dev | 0.00 | 1.79 | 1.73 | 1.81 |

(n = 66)

Example 2

Composition 1 liquid-expandable articles were tested acutely in a lethal porcine subclavian hemorrhage model against a control of Combat Gauze (CG), the current Special Operational Forces standard of care for severe hemorrhage.

Materials

Composition 1 liquid-expandable articles were prepared as described in Example 1. The mean thickness of the liquid-expandable article cylinders was 4.54 mm with a standard deviation 0.84 mm. Disposable syringes were modified to create applicators. Briefly, the tips were cut off 60 ml syringes and vinyl end caps were added. An X-pattern was cut into the end caps to allow passage of articles. One hundred liquid-expandable articles were loaded into each applicator.

Methods

A modified version of the published Institute of Surgical Research (ISR) swine femoral injury model served as a basis for the subclavian model (Kheirabadi B S, et. al, 4009). Sixteen crossbred Yorkshire castrated swine were used in this study. Prior to transection of the subclavian artery and vein, splenectomies were performed to promote coagulopathy. Wound cavity volume and depth, $CO_2$, $O_2$, mean arterial pressure, hemoglobin concentration, and vessel diameter were measured and recorded. Primary endpoints of the study included: Hemostasis at 4 minutes, hemostasis at 60 minutes, and survival at 60 min. A third-party medic from the Emergency Medicine Department at Madigan Army Hospital applied randomized treatment groups to minimize bias.

To create the injury, the artery, veins and nerve plexus were completely transected at middle section by the surgeon. The surgeon was blinded to the hemorrhaging site of the wound. After 30 seconds free bleeding the medic applied the treatment. The average pre-treatment 30-second blood loss for both treatment groups exceeded 700 cc. The medic was given 4 minutes to apply each product. Liquid-expandable articles were applied using applicators until the wound was filled to capacity, but no external pressure was applied. Per directions on CG packaging, a single CG dressing was used, backed with Kerlix to fill the wound cavity and external pressure applied.

Results

| Endpoint | Hemostatic Sponges | Combat Gauze | P-value |
|---|---|---|---|
| Hemostasis at 4 minutes | 6/8 (75%) | 2/8 (25%) | 0.03 |
| Hemostasis at 60 minutes | 8/8 (100%) | 2/8 (25%) | 0.007 |
| Survival at 60 minutes | 8/8 (100%) | 3/8 (37.5%) | 0.026 |

Example 3

Composition 2, 3 and 4 liquid-expandable articles were tested acutely in a lethal porcine subclavian hemorrhage model.

Materials

Liquid expandable articles were prepared as described in Example 1. The mean thickness of the Composition 2 samples was 3.0 mm with a standard deviation 0.43 mm. The mean thickness of Composition 3 samples 2.7 mm with a standard deviation 0.30 mm. The mean thickness of Composition 4 samples was 3.0 mm with a standard deviation 0.45 mm.

Disposable syringes were modified to create applicators. Briefly, the tips were cut off 60 ml syringes and vinyl end caps were added. An X-pattern was cut into the end caps to allow passage of articles. One hundred liquid-expandable articles were loaded into each applicator.

Methods

A modified version of the published Institute of Surgical Research (ISR) swine femoral injury model served as a basis for the subclavian model (Kheirabadi B S, et. al, 4009). Twenty-four crossbred Yorkshire castrated swine were used in this study. Prior to transection of the subclavian artery and vein, splenectomies were performed to promote coagulopathy. Wound cavity volume and depth, CO2, O2, mean arterial pressure, hemoglobin concentration, and vessel diameter were measured and recorded. Primary endpoints of the study included: Hemostasis at 4 minutes, hemostasis at 60 minutes, and survival at 60 min. A third-party medic from the Emergency Medicine Department at Madigan Army Hospital applied randomized treatment groups to minimize bias.

To create the injury, the artery, veins and nerve plexus were completely transected at middle section by the surgeon. The surgeon was blinded to the hemorrhaging site of the wound. After 30 seconds free bleeding the medic applied the treatment. The medic was given 4 minutes to apply each product. Liquid-expandable articles were applied using applicators until the wound was filled to capacity, but no external pressure was applied.

Results

| | Number of Test Animals Hemostatic at 4 min. | Number of Test Animals Hemostatic at 60 min. | Average blood loss at 30 s post injury (cc) | Number of Animals survived at 60 min |
|---|---|---|---|---|
| Composition 2 | 8/8 | 8/8 | Ave = 568.491 Std = 258.39 | 8/8 |
| Composition 3 | 6/8 | 7/8 | Ave = 707.798 Std = 161.7 | 7/8 |
| Composition 4 | 7/8 | 8/8 | Ave = 586.7 Std = 278.3 | 8/8 |

What is claimed is:

1. A hemostatic composition comprising a plurality of liquid-expandable articles, wherein:
    individual liquid-expandable articles of the plurality of liquid-expandable articles comprise a material compressed along a first axis, wherein the compressed material is non-oxidized cellulose;
    individual liquid-expandable articles are mechanically expandable into expanded articles upon contact with liquid such that mechanical expansion of the individual liquid-expandable articles is principally along the first axis; and
    individual liquid-expandable articles have a first dimension along the first axis, a second dimension along a second axis perpendicular to the first axis, and the first dimension of the individual liquid-expandable articles is less than the second dimension of the individual liquid-expandable articles.

2. The hemostatic composition of claim 1, further comprising:
    an expandable bag containing the plurality of liquid-expandable articles.

3. The hemostatic composition of claim 2, wherein the expandable bag is porous.

4. The hemostatic composition of claim 1, wherein the plurality of liquid-expandable articles comprises at least two liquid-expandable articles coupled together.

5. The hemostatic composition of claim 1, wherein an individual liquid-expandable article is mechanically expandable along the first axis into a corresponding individual expanded article having a third dimension along the first axis and a fourth dimension along the second axis, the first dimension is less than the second dimension, and the third dimension is greater than the fourth dimension.

6. The hemostatic composition of claim 1, wherein the individual liquid-expandable articles have a cylindrical shape.

* * * * *